United States Patent
Varaklis et al.

(10) Patent No.: US 9,412,161 B2
(45) Date of Patent: Aug. 9, 2016

(54) SYSTEMS AND METHODS FOR MEDICAL USE OF MOTION IMAGING AND CAPTURE

(75) Inventors: John Varaklis, Basel (CH); Craig Smith, Seattle, WA (US)

(73) Assignee: Novartis AG, Basel (CH)

(*) Notice: Subject to any disclaimer, the term of this patent is extended or adjusted under 35 U.S.C. 154(b) by 303 days.

(21) Appl. No.: 13/981,557

(22) PCT Filed: Jan. 23, 2012
(Under 37 CFR 1.47)

(86) PCT No.: PCT/EP2012/050994
§ 371 (c)(1),
(2), (4) Date: Feb. 11, 2014

(87) PCT Pub. No.: WO2012/101093
PCT Pub. Date: Aug. 2, 2012

(65) Prior Publication Data
US 2014/0153794 A1    Jun. 5, 2014

Related U.S. Application Data (60) Provisional application No. 61/436,074, filed on Jan. 25, 2011.

(51) Int. Cl.
| | |
|---|---|
| *G06K 9/00* | (2006.01) |
| *G06T 7/00* | (2006.01) |
| *A61B 5/11* | (2006.01) |
| *A61B 5/00* | (2006.01) |
| *G06F 19/00* | (2011.01) |
| *A61H 5/00* | (2006.01) |

(52) U.S. Cl.
CPC ............ *G06T 7/0012* (2013.01); *A61B 5/1124* (2013.01); *A61B 5/1128* (2013.01); *A61B 5/744* (2013.01); *G06F 19/3418* (2013.01); *G06F 19/3481* (2013.01); *A61H 5/00* (2013.01); *A61H 2201/5092* (2013.01)

(58) Field of Classification Search
None
See application file for complete search history.

(56) References Cited

U.S. PATENT DOCUMENTS

| | | |
|---|---|---|
| 5,752,621 A | 5/1998 | Passamante |
| 6,994,670 B2 | 2/2006 | Teicher et al. |
| 7,433,024 B2 | 10/2008 | Garcia et al. |

(Continued)

FOREIGN PATENT DOCUMENTS

| | | |
|---|---|---|
| CN | 101244027 A1 | 8/2008 |
| EP | 1749511 A1 | 2/2007 |

(Continued)

OTHER PUBLICATIONS

Matsukawa Tsuyoshi et al "Visualizing Physiological Condition of Two Persons during Cooperative Motion" 30th Annu Int IEEE EMBS Conf, Vancouver, British Columbia, Canada pp. 5176-5179 (Aug. 2008).

(Continued)

*Primary Examiner* — Li Liu
(74) *Attorney, Agent, or Firm* — Michael Mazza (57) ABSTRACT

A motion sensing and capture system to provide to a patient and/or healthcare provider, patient motion data and/or motion impairment data, which can be used as a diagnostic, predictive or therapeutic tool. Such method comprises the steps of: (a) selecting one or more patient motions; (b) using a sensing and capture system to image an initial set comprising the one or more motions to provide an initial set of motion data; and (c) conveying such initial set of motion data to a patient and/or healthcare provider.

7 Claims, 5 Drawing Sheets

(56) References Cited

U.S. PATENT DOCUMENTS

| | | | | |
|---|---|---|---|---|
| 8,187,209 | B1* | 5/2012 | Giuffrida | 600/595 |
| 8,781,856 | B2* | 7/2014 | Hanina et al. | 705/2 |
| 2003/0181790 | A1* | 9/2003 | David et al. | 600/300 |
| 2004/0002336 | A1 | 1/2004 | Wu et al. | |
| 2004/0002636 | A1* | 1/2004 | Teicher et al. | 600/300 |
| 2009/0299232 | A1 | 12/2009 | Lanfermann et al. | |
| 2010/0049095 | A1* | 2/2010 | Bunn et al. | 600/595 |
| 2010/0323991 | A1 | 12/2010 | Bar-Or | |
| 2011/0054870 | A1* | 3/2011 | Dariush | G06F 3/011 703/11 |
| 2011/0275051 | A1* | 11/2011 | Hanina et al. | 434/365 |
| 2013/0123684 | A1* | 5/2013 | Giuffrida et al. | 604/65 |

FOREIGN PATENT DOCUMENTS

| | | |
|---|---|---|
| JP | H08215177 A | 8/1996 |
| JP | 2006302122 A | 11/2006 |
| WO | 2012093163 A2 | 7/2012 |

OTHER PUBLICATIONS

Valin Myriam et al "Video Surveillance of Medication Intake" Proc 28th IEEE EMBS Annu Int Conf, New York City, USA pp. 6396-6399 (Aug. 2006).

International Search Report, PCT/EP2012/050994 (Nov. 8, 2012).

Written Opinion, PCT/EP2012/050994 (Jul. 30, 2013).

Matsukawa et al., "Visualizing Physiological Condition of Two Persons during Cooperative Motion", Engineering in Medicine and Biology Society, 2008, 30th Annual International IEEE EMBS Conference, pp. 5176-5179.

Valin et al., "Video Surveillance of Medication Intake", Engineering in Medicine and Biology Society, 2006, 28th Annual International Conference of the IEEE, pp. 6396-6399.

* cited by examiner

SYSTEMS AND METHODS FOR MEDICAL USE OF MOTION IMAGING AND CAPTURE

BACKGROUND

The present application relates generally motion sensing, imaging capture, and analysis, and the use thereof in the assessment and treatment of patients suffering from diseases or conditions resulting in motion impairment, as well as the use of motion sensing and capture to evaluate and diagnose symptomatic patients or asymptomatic subjects.

A number of diseases or conditions are known which exhibit neurological effects, or which affect or impact a patient's motion, or some aspect of movement. Parkinson's Disease, Lou Gherig's Disease (ALS), and cerebral palsy are well known examples. Other diseases and conditions are known which can impair motion or activity, such as COPD. Still other diseases and conditions may exhibit some effect on motion or activity, for example Autism, schizophrenia and Alzheimer's disease. Conversely, certain diseases and/or conditions may be detected and/or diagnosed by their affects on a patient's motion or physical activity.

In some cases, an ailment may affect a patient's activity level or range of activities by preventing the patient from being active. For example, chronic pain may cause a patient to avoid particular physical activities, or physical activity in general, where such activities increase the pain experienced by the patient. Other ailments that may affect patient activity include movement disorders such as tremor, Parkinson's disease, multiple sclerosis, epilepsy, or spasticity, which may result in irregular movement or activity, other neurological disorders, or a generally decreased level of activity. The difficulty walking or otherwise moving experienced by patients with movement disorders may cause such patients to avoid movement to the extent possible. Further, depression or other neoropsychiatric disorders such as dementia, depression, mania, bipolar disorder, or obsessive-compulsive disorder, or conditions such as congestive heart failure, cardiac arrhythmia, gastrointestinal disorders, and incontinence are other examples of disorders that may generally cause a patient to be less active. When a patient is inactive, he may be more likely to be recumbent, i.e., lying down, or sitting, and may change postures less frequently.

Appropriate therapeutic drugs or other therapeutic forms indicated for motor diseases and/or neurological conditions may be determined by assessment of one or more of patient neurologic behavior, gait and motor coordination and activity levels. In addition, these metrics are important measures of long-term functional recovery. However, assessing the degree of motor dysfunction in a patient, whether acutely or over a longer term, is a difficult challenge. Some methods involve subjective scoring, by a clinician, of objective findings. Other methods of assessing neurologic behavior include the measurement of motor coordination and skill acquisition using various tests. These are not suited for fine motor measurements. Moreover, these tests require the patient to personally visit a clinician or healthcare provider, and often require the patient to visit a variety of different clinicians or healthcare providers, and/or visit multiple times. Another drawback of existing tests is that they often require specialized equipment, such as sensors which physically attach to the patient (e.g. accelerometers, gyros, magnetometers, Hall effect sensors and the like), and/or dedicated computer processing systems.

In addition to the need by clinicians and/or healthcare providers to evaluate individual patient neurological functions, drug manufacturers often to perform neurological evaluations on a test group of patients in the course of clinical trials to determine the safety and efficacy of a new medical treatment, for example, a new drug. During these trials, the medical treatment is administered to subjects in a test group. These subjects are monitored to gather clinical research data associated with subjects before, during, and after administration of the medical treatment. Based on an analysis of the data collected from the test group, a determination can be made on whether or not the treatment is safe, effective, and suitable for sale to the general public. This approach further extends to the post-marketing phase of treatment, where real-world use data is also collected for a number of safety, efficacy, and cost-effectiveness use cases.

Accordingly, there is a need for a system, apparatus and method by which fine motor activity and/or impairment can be accurately determined. There is a further need for such a system, apparatus and method which can be used by the patient at the patient's home or office, and without the need for special or dedicated sensors or computer equipment, and which is readily usable by young and old patients alike.

There is additionally a need for a system, apparatus and method by which subjects or patients can be evaluated based upon physical presentation, and/or ability (or inability) to perform motions.

SUMMARY

The invention comprises a system, apparatus and method for capturing and analyzing movement and neurological coordination information or corresponding activity levels, from a patient, also sometime referred to herein as a subject. Embodiments of the invention further comprise a system, apparatus and method for capturing and analyzing movement and neurological coordination information including corresponding patient/subject activity levels. Embodiments of the invention further comprise a system, apparatus and method for capturing and analyzing movement and neurological coordination information including corresponding patient/subject activity levels contextualized by or with biomarkers, sensors and/or patient or stand-alone devices which act to facilitate at least one of data capture, storage, exchange or analysis.

Embodiments of the system comprise an automated intelligent computer system that captures and scores physical aspects including but not limited to subject motion, neurological coordination, gait and motor coordination, movement, flexion of limbs, position of limbs, reaction to stimuli, body posture, and physical appearance, e.g. major components of a neurological evaluation.

In one embodiment, the present invention comprises a method for capturing and evaluating motion data of a subject, comprising the steps of: (a) imaging a motion of a test subject; (b) capturing a set of data representing said motion by said subject; (c) processing said set of data, to yield a set of values associated with said subject; (d) generating a display of an avatar representative of said subject; and (e) causing a display of a visual indicator at a location associated with an anatomical component of the avatar representation, wherein the visual indicator represents at least a portion of the set of data representing said subject, and wherein the location is determined based at least in part on the at least a portion of the set of said processed data. The method may further comprise the step(s) of cueing the patient to perform a motion.

In one embodiment, the present invention comprises a therapeutic method comprising the steps of: (a) selecting one or more patient motions; (b) using a sensing and capture system to image an initial set comprising the one or more selected patient motions to provide an initial set of motion data; (c) conveying such initial set of motion data to a healthcare provider; and (d) providing to the patient a therapy based upon such initial set of motion data. The therapy may comprise a medication, physical therapy or both.

In one embodiment, the present invention comprises a method for capturing and evaluating motion data associated with a plurality of subjects, comprising the steps of: (a) receiving, by a computer processor, a set of imaging data associated with each of a plurality of subjects; (b) causing a display of an avatar representation of the plurality of subjects; (c) causing a display of a visual indicator at a location associated with an anatomical component of the avatar representation, wherein the visual indicator represents at least a portion of the set of imaging data representing at least two subjects of the plurality of subjects, and wherein the location is determined based at least in part on the at least a portion of the set of imaging data.

In one embodiment, the present invention comprises a method of evaluating a patient, the method comprising the steps of: (a) selecting one or more patient motions; (b) using a sensing and capture system to image an initial set comprising the one or more motions to provide an initial set of motion data; and (c) conveying such initial set of motion data to a healthcare provider.

In one embodiment, the present invention comprises a method of evaluating a patient or subject, the method comprising the steps of: (a) selecting one or more patient motions; (b) using a sensing and capture system to image an initial set comprising the one or more selected patient motions to provide an initial set of motion data; (c) conveying such initial set of motion data to the patient and/or a healthcare provider; and (d) providing to the patient a therapy based upon such initial set of motion data.

In one embodiment, the present invention comprises a method of evaluating a patient, the method comprising the steps of (a) selecting one or more patient motions; (b) using a sensing and capture system to image an initial set comprising the one or more motions to provide an initial set of motion data; (c) conveying such initial set of motion data to the patient and/or a healthcare provider; (d) providing to the patient a therapy based upon such initial set of motion data; (e) using the sensing and capture system to image a secondary set comprising the one or more motions to provide a secondary set of motion data, the secondary set following a period of time after initiating the therapy; (f) comparing the initial set with the secondary set and conveying the comparison to the healthcare provider; and (g) re-evaluating the therapy based upon the data comparison.

In one embodiment, the present invention comprises a medication compliance device comprising: (a) an imaging means for imaging a motion of a patient, said motion comprising administering a medication; (b) image capture means to capture a set of data representing said motion by said patient; (c) processing means to process said set of data, to yield a set of values associated with said patient; and (d) feedback means to deliver to said patent and/or caregiver and/or clinician a result of said administration motion.

In one embodiment, the present invention comprises a therapeutic system or kit comprising: (a) an imaging means for imaging a motion of a patient, said motion comprising administering a medication; (b) image capture means to capture a set of data representing said motion by said patient; (c) processing means to process said set of data, to yield a set of values associated with said patient; (d) feedback means to deliver to said patent and/or caregiver and/or clinician a result of said administration motion; and (e) a medication. In one embodiment, the therapeutic system or kit further comprises the medication compliance device as defined above and a medication for treating a disease state comprising a neurological effect, e.g. a neurological disorder. The therapeutic system or kit may further comprise a set of instructions on how to use the medication compliance device.

In one embodiment, the present invention comprises an apparatus and system for capturing and evaluating motion data of a subject, comprising: (a) a motion database, from which selecting, a motion appropriate to the subject's initial condition is selected; (b) a cueing means to generate a visual display or audio command (or both) to cue the patient to perform the selected motion; (c) an image capture device to image and capture a plurality of images comprising said motion of the subject; (d) a processing means to capture and process a set of data representing said motion by said subject; (e) data analytic software to analyze the set of data to yield a set of values associated with said motion of the subject; and wherein the processing means is used to generate results representative of at least a portion of said processed data. The results may be provided as feedback in any human-perceptible format, such as visually on a display, audible signal or both.

In one embodiment, the present invention comprises an assistive device, comprising: (a) an imaging means for imaging a motion of a subject; (b) capture means to capture a set of data representing said motion by said subject; (c) processing means to process said set of data, to yield a set of values associated with said subject; and (d) an effector means, mechanically linked to said patient and connected to said processing means to translate a set on values into an assistive motion.

In one embodiment, the invention comprises the use of a of a motion sensing and capture system comprising a motion database; an image capture device, a computer processor; data analytic software; and a human perceptible signal device, in the diagnosis of a human or animal condition. The diagnosis may be followed by a suitable treatment, such as administering a drug, pharmaceutical or nutraceutical, and/or by physical or exercise therapy, and/or by dietary changes.

In another embodiment, there is provided a diagnostic tool comprising a motion sensing and capture system comprising a motion database; an image capture device, a computer processor, and optionally a data analytic software.

In one embodiment, the invention is directed to techniques for evaluating a therapy (drug or physical or both) delivered to a patient. Based in whole or in part upon the results of the patient's motion analysis, the therapy parameter sets may change over time such that the therapy is delivered according to one or more therapy parameter sets which may be the same as or may differ from the initial therapy parameter sets. Thus, a patient's motion, motion impairment or posture events may be associated with a current therapy parameter set when the event is identified. A list of the therapy parameter sets and associated posture metrics may be delivered to the healthcare provider, such as clinician, for evaluation of the relative efficacy of the therapy parameter sets. In this manner, the healthcare provider may readily identify the therapy parameter sets that support the highest activity levels for the patient, and evaluate the relative efficacy of the parameter sets.

The therapy or medication may be designed to treat a neurological disorder of a human or animal patient. Example therapies may include a movement disorder therapy, psychological disorder therapy, dementia therapy or deep brain stimulation therapy. Specific neurological disorders may include Multiple Sclerosis, Parkinson's disease Alzheimer's disease or epilepsy.

In one embodiment, the apparatus, system or method herein may be useful for any state, condition or disease, or disease state, which may be detected, evaluated, diagnosed or treated by the effects on a patient's motion or physical activity. Such a disease may be a motion-implicated disease, may comprise a neurological effect, e.g. may be a neurological disorder, e.g. Multiple Sclerosis, Parkinson's disease Alzheimer's disease or epilepsy.

In one embodiment, the apparatus, system or method herein may be used for wellness monitoring, that is, in subjects that do not, or do not at an initial time, exhibit any symptoms of any state, condition or disease which may be detected, evaluated, diagnosed or treated by the effects on a patient's motion or physical activity, e.g. as hereinabove defined.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

In one embodiment, the invention comprises an automated system to measure motor function and effects thereon in patients. In another aspect, the invention can be of use for the assessment of motor function. The system of the invention allows for a more objective, faster and more consistent assessment of the degree of functional impairment and course of recovery or worsening of the condition, and this assessment can be applied to a variety of patient motions, including gait, breathing, eye movement, eye focus, tremors, and limb and coordinated appendage movement, and combinations thereof.

In one embodiment, the system has a resolution, and can detect movement, such as displacement, or motion range, of as little as 0.5 to 5 mm. In one aspect the system has a resolution of 1 to 4 mm. In one aspect the system has a resolution of 2 to 3 mm. In one aspect the system has a resolution of 1 to 2 mm.

In one embodiment, the invention comprises a motion capture system which further comprises computer vision, which permits an objective assessment of movement function using three-dimensional imaging and capture techniques. Thus, capture of anatomical positioning includes, but is not limited to, human or animal kinematics, dynamics, ergonomics, biomechanics, movement, shape and position.

In one embodiment, the present invention comprises a computing system which can model and display a visual representation of a patient in a physical space. The system comprises a capture device that captures image data of a scene and a monitor that displays a visual representation that corresponds to the patient. For example, a camera-controlled computing system may capture patient image data, generate a model of the patient, and display a visual representation of that model. The system may track the patient in the physical space such that the visual representation maps to the patient or the motion captured in the physical space. Thus, the motion of the visual representation is representative of the movement of the motion of the patient in the physical space. For example, the visual representation of the patient may be an avatar displayed on a screen, and the avatar's motion may correspond to the patient's motion. In some embodiments it may be useful to display motion results as single patient at a single time point or as a single patient over time, and/or as an aggregate of patients or a network of patients.

A patient's motion in the physical space may be tracked, modeled, stored and/or displayed. Patient motion data, or elements thereof may be stored in a device memory and compared with the same motion data, or elements captured at different times. The system may generate a differential comparison of the data for presentation to a clinician and/or to the patient. The clinician may thus better evaluate the results of a particular therapeutic regime, i.e. of a particular medication, or to prescribe a new or different therapy.

The collected data may be analyzed and displayed using a means for electronically displaying medical data, including clinical research data, from multiple subjects, such as an avatar body mapping display and analysis system as described, for example, in co-pending PCT/EP2012/050160 filed 5 Jan. 2012, and entitled: DISPLAY OF CLINICAL RESEARCH DATA USING AN AVATAR.

In some embodiments, the data captured by the capture device is presented in the form of an avatar, or another virtual object that corresponds to the subject (e.g. patient) in the physical space. It may be desirable to initialize and/or customize a visual representation based on actual characteristics of the subject. For example, the capture device may identify physical features of a subject and customize the subject's avatar based on those identified features, such as height, weight, morphology, feature shape, and the like.

In some embodiments the avatar or virtual object in the virtual environment may be provided with interactions similar to, or as a proxy or surrogate for interactions in the physical space. For example, a virtual a healthcare provider may be generated and may provide diagnosis, results, suggestions or feedback to the patient avatar based in whole or in part upon the data obtained by the system, and/or any adjunct data (such as sensor data or lifestyle data). This may comprise the use of one or more algorithms to act on the data. In one embodiment, the feedback may take the form of coaching for the avatar, such as diet guidelines, that can be graphically or pictorially or verbally represented, and which the physical patient can then act upon.

The system and method may track the subject and any motion in the physical space over time and apply modifications or updates to the avatar (or other presentation form) based on the history of the tracked data. Aspects of a skeletal or mesh model of a person may be generated based on the image data captured by the capture device to represent the subject's body type, bone structure, height, weight, or the like.

To generate a model representative of a target or object in a physical space, a capture device can capture a depth image of a scene wherein a human or animal subject is present. In one embodiment, the capture device may determine whether one or more targets or objects in the scene correspond to a human target such as the subject. For example, a target identified as a human may be scanned to generate a skeletal model associated therewith. The skeletal model may then be provided to the computing system for tracking the skeletal model and rendering an avatar associated with the skeletal model. The computing system may determine which controls to perform in an application executing on the computer system based on, for example, motions of the user that have been recognized and mapped to the skeletal model. An animal may be represented in an analogous manner.

The system, apparatus methods, and components of avatar creation and customization described herein may be embodied in a computing system or multi-media console, such as a gaming console, in which it is desired to display a visual representation of a target, including, by way of example and without any intended limitation, satellite receivers, set top boxes, arcade games, personal computers (PCs), portable telephones, personal digital assistants (PDAs), smartphones, notebook computers and other personal and/or hand-held and/or fixed computing devices.

Various embodiments are described herein relating to interfaces for displaying motion and/or medical data obtained by the motion recognition, capture analysis, and tracking system herein. The interfaces may include an avatar for displaying a set of medical data, including clinical research data, associated with a set of subjects. Visual representations of at least a portion of the set of medical data may be displayed with the avatar on or near a portion of the avatar associated with the at least a portion of the set of medical data.

The interfaces may be used by a patient, subject of a clinical trial, physician, health-care provider, relative, friend, researcher, etc. Additionally, access management functions may be provided to provide different levels of access to different users. For example, a physician may be provided with complete access, such as using one access permission setting, while a researcher may be provided more limited access, such as using another access permission setting.

In one embodiment, the motion analysis results are electronically transmitted to the healthcare provider, such as clinician. In one embodiment, the motion analysis results are provided to the patient (or subject) in real-time, or nearly real-time. In one embodiment, the motion analysis results are provided to both the healthcare provider and patient (or subject).

Figure 1A:
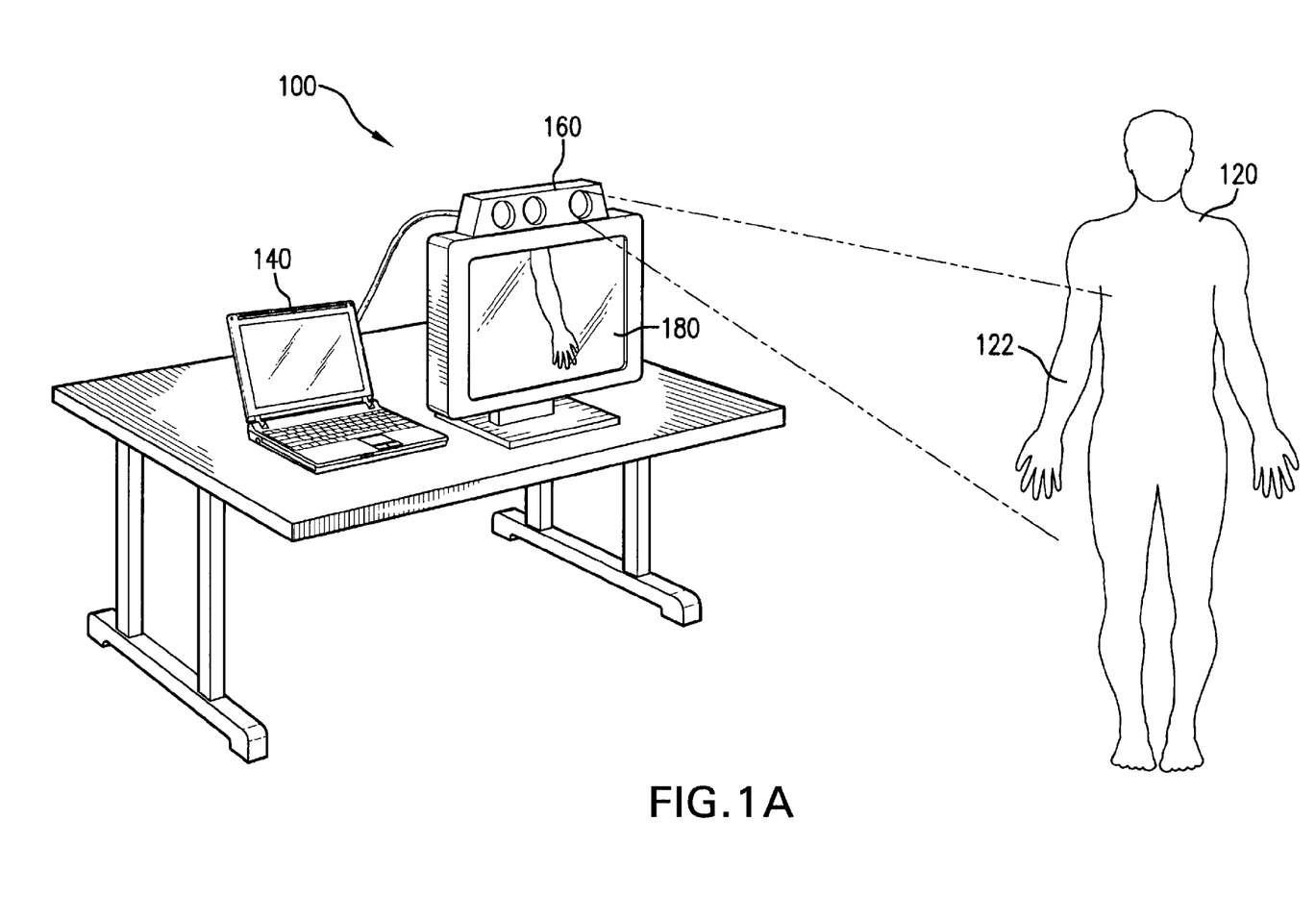
FIGS. 1A and 1B illustrate an exemplary motion sensing and capture interface and system for capturing and analyzing a patient's motion.
Figure 1B:
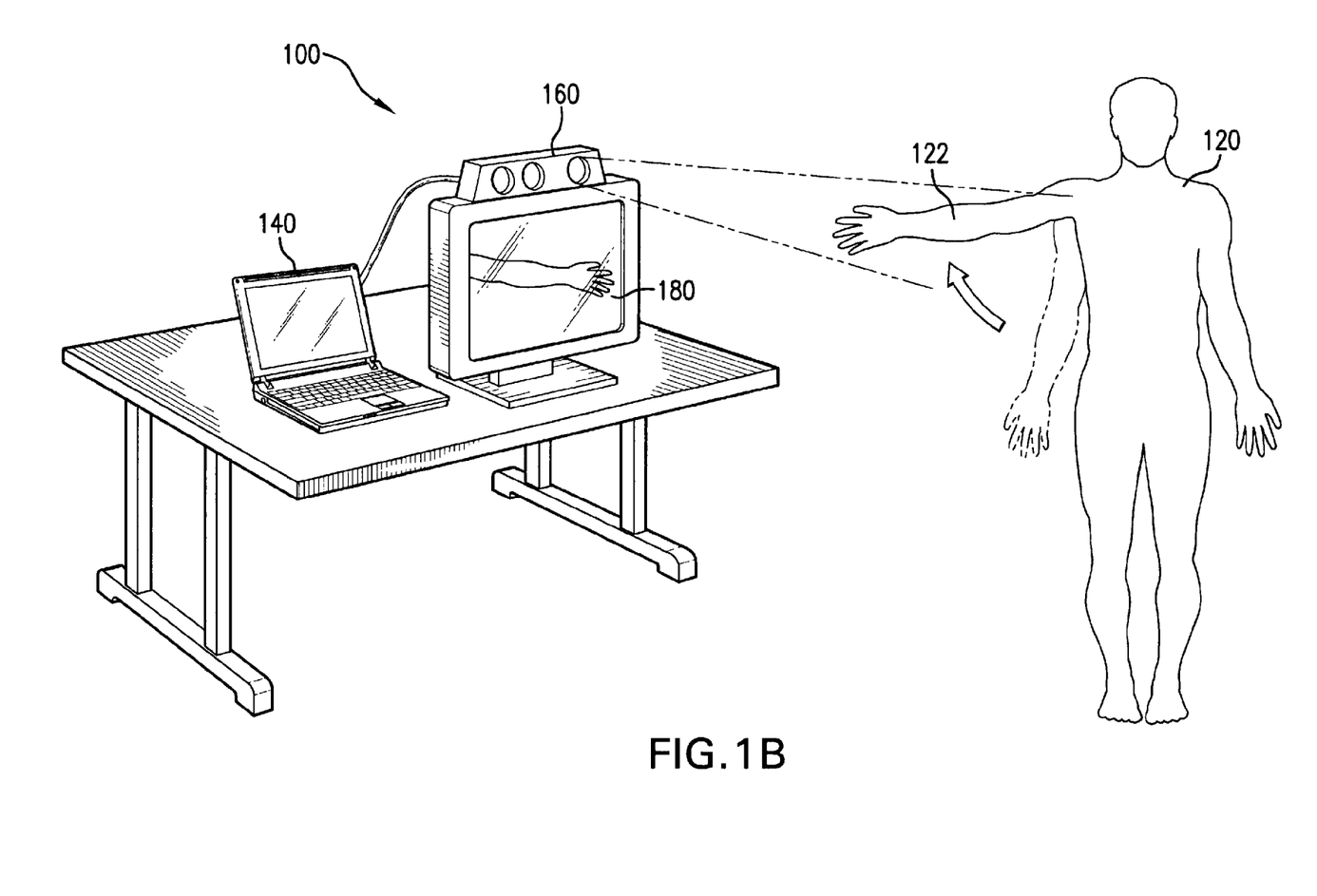

FIGS. 1A and 1B illustrate an example embodiment of a configuration of a patient motion recognition, capture analysis, and tracking system 100. In the example embodiment, a patient 120 is being recognized, sensed, imaged, and tracked with particular reference to the arm 122, and/or specific components of the arm 122, such as forearm, fingers etc. The system 100 may gather information related to the patient's movements in the physical space.

The motion recognition, capture analysis, and tracking system 100 may comprise a computing system 140. The computing system 140 may be a computer, a gaming system or console, or the like. The computing system 140 may include hardware components and/or software components such that the computing system 140 may be used to execute the motion recognition, capture analysis, and tracking application described herein.

The motion recognition, capture analysis, and tracking system 100 may further comprise an image capture device 160, for example, a camera or cameras, that may be used to visually monitor the patient 120, such that motions may be captured, analyzed, and tracked.

According to one embodiment, the motion recognition, capture analysis, and tracking system 100 may be coupled to a video display 180 that may provide visual feedback and/or visual input cues to the patient 120. The visual display may comprise a television, a computer monitor, a high-definition television (HDTV), a 3D television, and may be monochromatic or color. The computing system 140 may include a video adapter such as a graphics card and/or an audio adapter such as a sound card that may provide audiovisual signals associated with an application running on the computing system. According to one embodiment, the video display 180 may be connected to the computing system 140 via any suitable connection means known to the art. In a preferred embodiment, the system 100 is capable of both video and audio inputs and outputs.

In embodiments of the invention that patient feedback and/or motion cueing may be provided to the patent by video or image means, as by an avatar or visual representation on the display 180, or by audio means only, such as by audible verbal instructions, or a tone or series of tones, or by both audio and visual means.

Sounds, both patient-made and ambient, may be captured by the system 100, through a microphone or other audio sensor (not shown) and processed by the computing system 140. Appropriate filters may be implemented in software, hardware or firmware, such that certain sounds are selected which correspond to aspects of the patient's condition. These sounds may be processed and form part of the data set. The sound data may be adjunctive to the motion capture data, contextual thereto, or independent therefrom. The sound data may be used in any way described for any of the other data herein, thus can be used or to assist in any identification, determination, diagnosis, prognosis, evaluation, prediction, assessment or therapy. In one example, where a patient is suspected of having a respiratory disease, such as COPD, or diagnosed with COPD, sounds, such as breathing sounds, may assist in analysis, management or therapy.

In some embodiments, sound may be used independently as a means by which the patient or subject may command the system, such as initiating a motion capture. Voice (or audio) commands may be used to trigger system workflow, as for example, by permitting the subject or patient to start, stop, navigate or activate menus, features or screens of the system. In some embodiments, voice recognition may be used to verify the identity of the subject or patient using the system.

As further shown in FIG. 1B, the motion recognition, capture analysis, and tracking system 100 may be used to recognize, analyze, and/or track motions performed by the patient 120. For example, in FIG. 1B the patient is depicted as moving his arm 122 in response to a cue from the system 100 to do so. The motion is tracked using the image capture means or device 160 such that the motion may be analyzed. Thus data, comprising a plurality of signals from the image capture device, is processed and/or correlated to result in an output.

Figure 2:
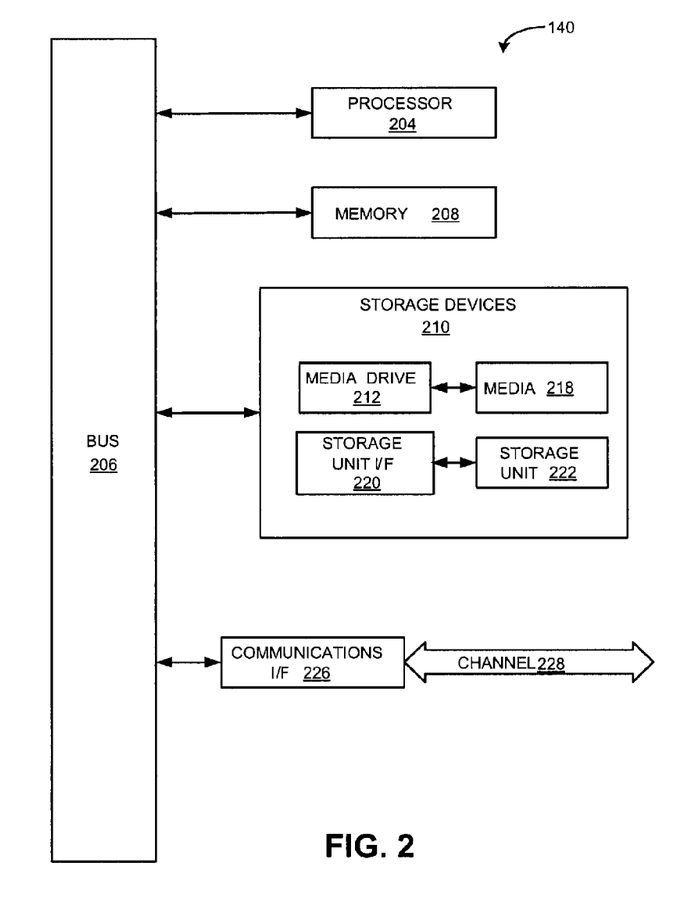
FIG. 2 illustrates an exemplary computing system that may be used to implement some or all processing functionality of various embodiments herein.

FIG. 2 is a block diagram illustrating an exemplary computing means or system 140 that may be employed to implement processing functionality for various aspects of the current technology (e.g., as a user/client device, media server, media capture server, media rules server, rules store, media asset library, activity data logic/database, gaming console, combinations thereof, and the like). Those skilled in the relevant art will also recognize how to implement the current technology using other computer systems or architectures. Computing system 140 may comprise, for example, a user device such as a desktop, mobile phone, personal entertainment device, cameras, microphones, DVR, medicament dispensing device, and so on, a mainframe, server, or any other type of special or general purpose computing device as may be desirable or appropriate for a given application or environment. In some embodiments herein, computing system 140 comprises gaming functionalities. Computing system 140 can include one or more processors, such as a processor 204. Processor 204 can be implemented using a general or special purpose processing engine such as, for example, a microprocessor, microcontroller or other control logic. In this example, processor 204 is connected to a bus 206 or other communication medium.

Computing system 140 can also include a main memory 208, such as random access memory (RAM) or other dynamic memory, for storing information and instructions to be executed by processor 204. Main memory 208 also may be used for storing temporary variables or other intermediate information during execution of instructions to be executed by processor 204. Computing system 140 may likewise include a read only memory ("ROM") or other static storage device (not shown) coupled to bus 206 for storing static information and instructions for processor 204.

The computing system 140 may also include information storage mechanism 210, which may include, for example, a media drive 212 and a removable storage media 218. The media drive 212 may include a drive or other mechanism to support fixed or removable storage media, such as a hard disk drive, a floppy disk drive, a magnetic tape drive, an optical disk drive, a CD or DVD drive (R or RW), or other removable or fixed media drive. Storage media 218 may include, for example, a hard disk, floppy disk, magnetic tape, optical disk, CD or DVD, or other fixed or removable medium that is read by and written to by media drive 212. As these examples illustrate, the storage media 218 may include a computer-readable storage medium having stored therein particular computer software or data.

In alternative embodiments, information storage mechanism 210 may include other similar instrumentalities for allowing computer programs or other instructions or data to be loaded into computing system 140. Such instrumentalities may include, for example, a removable storage unit 222 and an interface 220, such as a program cartridge and cartridge interface, a removable memory (for example, a flash memory or other removable memory module) and memory slot, and other removable storage units 222 and interfaces 220 that allow software and data to be transferred from the removable media unit 218 to computing system 140.

Computing system 140 can also include a communications interface 226. Communications interface 226 can be used to allow software and data to be transferred between computing system 140 and external devices. Examples of communications interface 226 can include a modem, a network interface (such as an Ethernet or other NIC card), a communications port (such as for example, a USB port), a PCMCIA slot and card, etc. Software and data transferred via communications interface 226 are in the form of signals which can be electronic, electromagnetic, optical, or other signals capable of being received by communications interface 226. These signals are provided to communications interface 226 via a channel 228. This channel 228 may carry signals and may be implemented using a wireless medium, wire or cable, fiber optics, or other communications medium. Some examples of a channel include a phone line, a cellular phone link, an RF link, a network interface, a local or wide area network, and other communications channels. Essentially any physical layer connectivity and communications protocol may be employed. In some embodiments, signals are conducted wirelessly, and may employ any suitable carrier frequency, modulation scheme and protocol, such as BlueTooth, ZigBee, CDMA, GSM and the like. Data may be stored and accessed in any manner known to the art, including local storage, remote servers and cloud computing.

In this document, the terms "computer program product" and "computer-readable storage medium" may be used generally to refer to media such as, for example, memory 208, storage device 218, or storage unit 222. These and other forms of computer-readable storage media may be involved in providing one or more sequences of one or more instructions to processor 204 for execution. Such instructions, generally referred to as "computer program code" (which may be grouped in the form of computer programs or other groupings), when executed, enable the computing system 140 to perform features or functions of embodiments of the current technology.

In an embodiment where the elements are implemented using software, the software may be stored in a computer-readable storage medium and loaded into computing system 140 using, for example, removable storage drive 210, drive 212 or communications interface 226. The control logic (in this example, software instructions or computer program code), when executed by the processor 204, causes the processor 204 to perform the functions of the technology as described herein.

In one embodiment, computing system 140 is configured to comply with applicable regulatory requirements of health authorities. For example, in the US, computer system 140 can implement appropriate encryption technology to comply with the Food and Drug Administration's regulations on electronic records as set forth in FDA 21 CFR Part 11.

It will be appreciated that, for clarity purposes, the above description has described embodiments of the technology with reference to different functional units and processors. However, it will be apparent that any suitable distribution of functionality between different functional units, processors or domains may be used without detracting from the technology. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

In one embodiment, the system 100 herein employs a speckle decorrelation method as described, for example, in U.S. Pat. No. 7,433,024, the disclosure of which is incorporated herein by reference for all purposes. Such a method uses a light source (typically a laser, emitting in the infrared range) and encodes information in emitted light patterns. One or more receiving camera(s) (typically a CCD or CMOS device) analyzes a deformation of those patterns by the object being sensed. Processing algorithms track the body's locations and movements, multiple times per second.

In some embodiments of the present invention, the receiving image capture device (camera or other sensing device) may receive images from multiple directions and/or from multiple viewpoints. Other receiving cameras or image capture devices potentially suitable herewith include quantum nanodot cameras, and ultrasonic sensors (used with ultrasound emissions as the imaging medium). While visible light is an exemplary media for image capture, the invention herein is not limited to such use, and other forms of imaging radiation (e.g. infrared, sonic, ultrasonic and the like) are suitable. In some embodiments of the present invention, motion is repeatedly imaged.

In one embodiment, the system 100 uses structured light, that is, the projection of a light pattern (plane, grid, or more complex shape) at a known angle onto an object. This technique is known for imaging and acquiring dimensional information. The most often used light pattern is generated by fanning out a light beam into a sheet-of-light. When a sheet-of-light intersects with an object, a bright line of light can be seen on the surface of the object. By viewing this line of light from an angle, the observed distortions in the line can be translated into height variations. Scanning the object with the light constructs 3D information about the shape of the object.

Several structured light capture systems, and pattern recognition software and protocols are known and described in the literature, and potentially suitable as the capture system herein. These include invisible structured light (ISR); infrared structure light (IRSL); and filtered structure light (FSL).

In one embodiment, the motion sensing, recognition and capture system of the present invention comprises a touch-free gaming device controller device sold by the Microsoft Corporation, Redmond Wash., under the tradename "Kinect™". Such a device comprises a relatively lightweight, portable imaging capture device that is designed and intended for consumer home use in the gaming space. As such, it interacts with a gaming console and a video display, e.g. television. This device is understood to build a dynamic wireframe representation, or skeletal map of the subject's body, which is then tracked to recognize movement. In one or more embodiments, the gaming device controller is coupled to a gaming console or computer, such as the XBOX™ controller sold by the Microsoft Corporation, Redmond Wash.

In another embodiment, a "time-of-flight" method may be used for the motion sensing and capture. In this method, infrared light (or the equivalent: invisible frequencies of light) are sent out into a 3D space, and then the time and wavelengths of light returned to the specially-tuned cameras are analyzed to reproduce the imaged space.

In one embodiment, multiple capture devices 160 (or the sensing elements thereof) may be employed. In embodiments of the invention, multiple capture devices 160 are used to capture a larger event space than can be captured by a single device. For example, multiple devices 160 may be spaced about an oval racetrack so that a subject's running motion is tracked throughout. In such a case, the devices 160 could be arrayed within the interior of the oval. Linear, horizontal or vertical arrangements of the devices 160 are also contemplated. The devices could be coupled to a single computing system 140, or multiple computing systems 140. One of more of the devices 160 may be movement driven, additionally or alternatively, to one or more fixed devices 160.

In one embodiment, multiple devices 160 may be arrayed about a central point, such that higher resolution of imaging within a single event area is achieved, and/or a three hundred and sixty degree capture area is achieved. For patient home use, multiple devices 160 (with associated computing systems 140, or single computing system 140) can be placed in different rooms to enable patient tracking as the patient moves from room to room. Such multiple devices may provide significant benefits in healthcare management for the elderly, for example. Multiple devices 160 may be set to have the same imaging and/or capture configuration, or may be set to have different imaging and/or capture configurations, the latter of which may aid in differential analyses. In some embodiments, the use of multiple and/or differential devices 160 and/or computing systems 140 may facilitate psychiatric evaluations, diagnoses and/or treatments of patients.

In one embodiment, the system 100 is provided with a sensor (not shown) to determine exactly the subject's or patient's distance from the capture device 160. Such a sensor may be implemented with an ultrasound transceiver or transducer and detector. In some embodiments, ultrasound may be additionally or alternatively used to implement the motion imaging and capture.

In one embodiment, the system 100 comprises a computer program, which may comprise a hardware embodiment, a software embodiment. The present invention may comprise a computer program product e.g. software stored in any tangible medium of expression having computer-usable program code stored in the medium.

Computer program code for carrying out operations of the present invention may be written in any individual or a combination of programming languages, and the program code may execute entirely or partially on the computing system 140, and/or entirely or partially on a remote computing system, connected to the system 100 by appropriate network or physical connection.

In one embodiment, the system 100 comprises system and/or process control software.

In one embodiment, the system and/or process control software comprises operating system software, which may be appurtenant to the computing system 140 and/or device 160.

In one embodiment, the system 100 comprises analytical software.

In one embodiment, the analytical software comprises a storage means for storing a plurality of data corresponding to a plurality of distinct data points and/or layers; a processing means for analyzing and selecting one or more distinct data points and/or layers; and a display means for representing the plurality of distinct data points and/or layers as a human perceptible display.

In one embodiment, the analytical software comprises data analytical software. In one embodiment, data analytics are carried out by ontology mapping. In one embodiment the concepts of ontology are used to compute concepts vectors for data records. The coordinates of the concept vectors may represent scores of the concepts of aspects of or fields within the data record(s). Scores, such as values, such as scalars, may be used to indicate the relevance of the respective concept for the data record according to a predefined measure. Such measure may be, for example, a probability, or other standardized measure in information retrieval. Appropriate databases store relevant data.

In one embodiment a similarity network is used to represent similarities between the data records. The similarity network unit may use as input the concept vectors and at least one relationship of the ontology. The similarity network unit may use a predefined algorithm, function or method for computing the similarity values of the edges of the similarity network.

In one embodiment a first set of data relates to a virtual model of the subject. A second set of data records may represent data pertaining to characteristics of an individual subject, such as a human or animal patient.

Additional elements of the system 100 may include various script codes, drivers (open and/or closed source), and various hardware or firmware components. Suitable algorithms for the system 100, the device 160, the computing system 140, or any subsystems of any of the foregoing may be implemented in hardware, software or firmware.

Methods

The system 100 may identify a posture event or a plurality of posture events based upon a plurality of image capture signals. In some embodiments, the system 100 periodically identifies the posture of the patient based on one or more signals, and the identified posture is stored as a posture event.

The system 100 may identify whether the patient is upright or recumbent, e.g., lying down. In some embodiments in which sensors are located at a plurality of positions on or within the body of the patient, the system 100 may be able to identify additional postures, such as standing, sitting and recumbent. Example locations for the sensors include on or with the trunk of the patient, e.g., within an implantable medical device in the abdomen of the patient, and additionally, in some embodiments, on or within an upper leg of the patient. In some embodiments, the system 100 identifies transitions between postures, and stores indications of posture transitions as posture events.

The system 100 may identify a subject's gait based upon a plurality of image capture signals. In some embodiments, the system 100 periodically identifies a gait of the patient based on the plurality of signals, and the identified gait is stored as a gait event. In some embodiments a library of gaits is developed by identifying gaits of a plurality of subjects and patients having a range of motion-implicated disease states as well as no disease states (i.e. motion-healthy subjects).

In one embodiment, the present invention comprises the use of a motion sensing and capture system to provide to set comprising one or more of a patient, a healthcare provider, and a clinician, patient motion data and/or motion impairment data, which data can then be used as a diagnostic tool. Such method comprises the steps of: (a) selecting one or more patient motions; (b) using a sensing and capture system to image an initial set comprising the one or more motions to provide an initial set of motion data; and (c) conveying such initial set of motion data to a healthcare provider.

In one embodiment, the present invention comprises the use of a motion sensing and capture system to provide to a set comprising one or more of a patient, a healthcare provider, and a clinician, patient motion data and/or motion impairment data, which can then be used as a tool, e.g. a diagnostic tool. Such method comprises the steps of: (a) selecting one or more patient motions; (b) using a sensing and capture system to image an initial set comprising the one or more selected patient motions to provide an initial set of motion data; (c) conveying such initial set of motion data to a healthcare provider; and (d) providing to the patient a therapy based upon such initial set of motion data.

In one embodiment, the present invention comprises the use of a motion sensing and capture system to provide to a set comprising one or more of a patient, a healthcare provider, and a clinician, patient motion data and/or motion impairment data, which can then be used as a diagnostic tool. Such method comprises the steps of: (a) selecting one or more patient motions; (b) using a sensing and capture system to image an initial set comprising the one or more motions to provide an initial set of motion data; (c) conveying such initial set of motion data to a healthcare provider; (d) providing to the patient a therapy based upon such initial set of motion data; (e) using the sensing and capture system to image a secondary set comprising the one or more motions to provide a secondary set of motion data, the secondary set following a period of time after initiating the therapy; (f) comparing the initial set with the secondary set and conveying the comparison to the healthcare provider; and (g) re-evaluating the therapy based upon the data comparison.

In one embodiment, the present invention comprises the use of a motion sensing and capture system to provide information to a set comprising one or more of a patient, a healthcare provider, and a clinician. The information comprises patient motion data and/or motion impairment data, which can then be used as a tool, e.g. a diagnostic tool, for one or more of the following: (i) the assessment of the existence a variety of states, diseases and conditions, including but not limited to various physical states, neurological conditions and psychological conditions; (ii) the assessment or evaluation of various physical states, neurological conditions and psychological conditions; (iii) the assessment or evaluation of the progress of various physical states, neurological conditions and psychological conditions; (iv) the diagnosis and/or prognosis of various physical states, neurological conditions and psychological conditions; and (v) performing a therapeutic intervention with respect to the various physical states, neurological conditions and psychological conditions. Such method comprises the steps of: (a) selecting one or more patient motions; (b) using a sensing and capture system to image an initial set comprising the one or more selected patient motions to provide an initial set of motion data; (c) conveying such initial set of motion data to the patient, healthcare provider or clinician; (d) analyzing said data set; and (e) providing feedback to the patient, healthcare provider or clinician based upon such initial set of motion data, and optionally (f) re-evaluating the therapy based upon the motion data.

Figure 3:
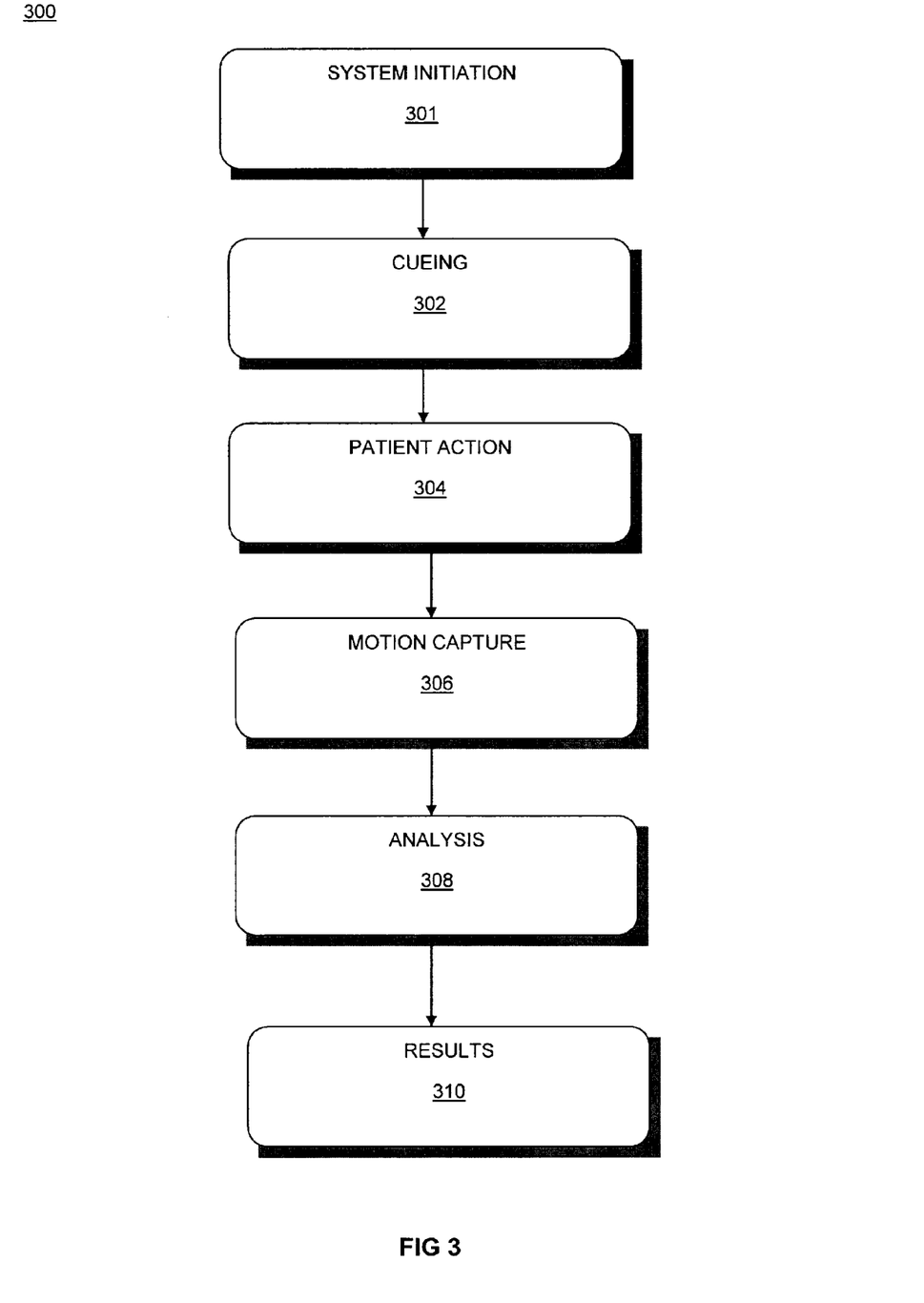
FIG. 3 is a diagrammatic process flow according to one embodiment of a method of the present invention.

FIG. 3 is a block diagram flowchart representing steps of one embodiment 300 of the motion recognition, capture analysis, and tracking system of the present invention. In the method of FIG. 3, the patient or subject initiates the system in block 301. Block 302 represents a cue step wherein the system provides an audible or visual instruction, or both, to the patient, such as "lift your right arm." The patient then complies with some action, in block 304, and the system captures the motion 306. Block 308 represents the analysis step. In this step the motion may be analyzed according to a number of protocols, singly or collectively. Motions which may be recorded and analyzed, include, but are not limited to: a range of motion, a speed of motion, acceleration or deceleration of a body part or the entire body, a smoothness or fluidity of motion, a direction of motion, tremors or vibrations, oscillations, rotary or rotational motions, linear motions, orbital or radial motions (such as eye motions), combination of any of the foregoing, and a change in any of the foregoing. In some embodiments, expressions, such as facial expressions, gestures and postural or body language may be captured, analyzed or contextualized. The recorded motion or motions may be saved, compared to prior results to arrive at a differential result, or analyzed independently. In Block 310, results of the motion capture and/or analysis may be displayed (tangibly such as printed, or intangibly, such as a screen display) for the patient, and/or a patient relative or friend, uplinked (or uploaded) to a healthcare provider or clinician or medical researcher. In one embodiment, as noted previously, the data and/or analysis may be supplied to a virtual healthcare provider or researcher. The results may be displayed in text or numerical form, in graphic form, or otherwise. In one embodiment, presentation of the results utilizes an avatar and body mapping program such as described in the previously cited PCT Patent Application titled: DISPLAY OF CLINICAL RESEARCH DATA USING AN AVATAR. Results may be displayed in one form for the patient and/or patient relative and in the same or different form for the healthcare provider and/or clinician. It should be noted that the display and analysis steps 308 and 310 may occur in any order, or simultaneously. In some embodiments of the present invention, one or more of the cue step 302, compliance step 304 and capture step 306, may be repeated multiple times before an analysis step 308 is conducted.

Results of the motion capture and/or analysis may be saved in a database, such as a personal health record or electronic health record. Such a database can store individual patient data, and can be used as well to review and analyze aggregate data, such as a single patient over time, or multiple patients (at a single time point, or over time). Of particular usefulness are means of manipulating the data to reveal correlates of change over time. As a non-limiting example, a patient with Autism may be monitored with the system 100. In one embodiment, an initial monitoring session may be conducted such that the patient motions are imaged and captured. Based upon a data set which at least in part comprises the monitoring data, a healthcare provider and/or clinician may direct the patient to perform a task or set of tasks, such as a simple or complex video game, or a set of repetitive tasks. This game may be supplied by the system 100, and displayed on the video device 180. As an example, in a system cueing step (e.g. 302), the patient may be instructed to stack or line up (on-screen) objects. The motions are imaged by the system 100, and may be recorded and a set of data generated. The data may be subjected to various analytical schemes, such as comparing a subset of motions at an initial time point with the same or similar subset of motions at a later time point. The comparison may be performed with a subset of the data, or substantially all of the data. The data may further be contextualized based upon data obtained from the patient's daily activities, such as diet or sleep. A healthcare provider and/or clinician may receive the raw and/or analyzed data, such as uploaded via the internet or phone system, and may be in the form of an avatar presentation. The healthcare provider and/or clinician may then attempt to modify the patient's behavior by some form of therapeutic intervention, such as a medicament, physical therapy or an environmental stimulus. The environmental stimulus may be an interactive game which the patient may play using the system 100. The process of imaging, analyzing and intervening may be repeated as often as necessary or useful.

In some embodiments, the system 100 is capable of directly supplying a therapy to a patient, such as an Autistic patient. In some embodiments of the invention, the system 100 may supply a therapy in the form of exercises or tasks requiring voluntary muscle control.

In some embodiments, the system 100 may conduct the cueing steps, imaging steps and analysis steps as above, and select an intervention, such as an interactive game, based upon the data collected and one or more treatment algorithms stored on the computing device 140. The system 100 thus acts as a closed-loop healthcare provider, without further actions on the part of a human clinician In one embodiment a musical instrument, such as a piano or piano keyboard, is displayed on the video device 140. The system 100 may instruct the patient to play the piano virtually, as by making motions with the hands and fingers which correspond to keys shown on the video display 180. The patient may be provided audio feedback from the audio portion of the system 100 such that the patient hears notes which are played. The motion of the patient playing the virtual keyboard is captured by the capture device 160 and may be analyzed to generate a data set which then can be used, as stated above, either by the healthcare provider and/or clinician, or which can be used by the system 100 to directly provide any therapeutic intervention to the patient. In some embodiments of the present invention, the therapeutic intervention comprises the playing of the music itself. In this aspect of the present invention, the analysis and intervention may comprise the same set of action.

In another aspect of the present invention, a patient may be provided speech therapy by the system 100. This can be done in the nature of a karaoke-type apparatus wherein words or characters appear on the screen and may be accompanied by audible words, speech, and/or music. The speech therapy or vocal therapy may comprise either the analysis, or the intervention, or both.

In some embodiments, the data (single patient or multiple patients) may be further contextualized by associating with other forms of patient data, such as other sensor data, patient reported data, adverse event data, biomarker data, or combinations thereof. Instrumented data may include accelerometer or other sensor data for patient positioning. It may be useful to supply as an adjunct to the image motion capture data, and may thus help to contextualize the motion data, other forms of data, such as, but not limited to, patient activity data, such as lifestyle characteristics, diet, sleep cycles, food and water consumption, telephone or wireless device use, computer use, social networking use, and the like.

In embodiments of the present invention motion imaging and capture steps may be performed multiple times, with or without therapy, and with or without direct healthcare provider feedback. While an advantage of the system of the present invention is that the motion sensing and analysis can be performed by the patient, at home, and at times suitable to the patient, the system may alternatively or additionally be used in the clinician's office or heath care facility. Motions which the patient may perform for capture by the system may depend upon the nature of the disease or condition being evaluated, diagnosed, or suspected, the affected body or anatomical part frequency of movement and degree of movement. The system may be programmed by the clinician to direct the patient to perform a particular motion for capture. This direction may come as an audio command, or by a representation on the video display (such as a avatar) which the patient is asked to emulate, or both. Thus, the patient may be directed to act as if he or she is catching a ball, by audio command, by depiction of the avatar catching a ball, or both.

In one embodiment, the present invention comprises a motion sensing and capture system to provide to a medical researcher patient motion data and/or motion impairment data, which can then be used as a research tool. Such method comprises the steps of: (a) selecting one or more patient motions; (b) enrolling a plurality of patients; (c) using a sensing and capture system to image an initial set comprising the one or more selected patient motions to provide an initial set of motion data, the set comprising aggregate data from the plurality of patients; (d) conveying such initial set of motion data to a medical researcher; and (e) evaluating possible therapies based upon such initial set of motion data.

Figure 4:
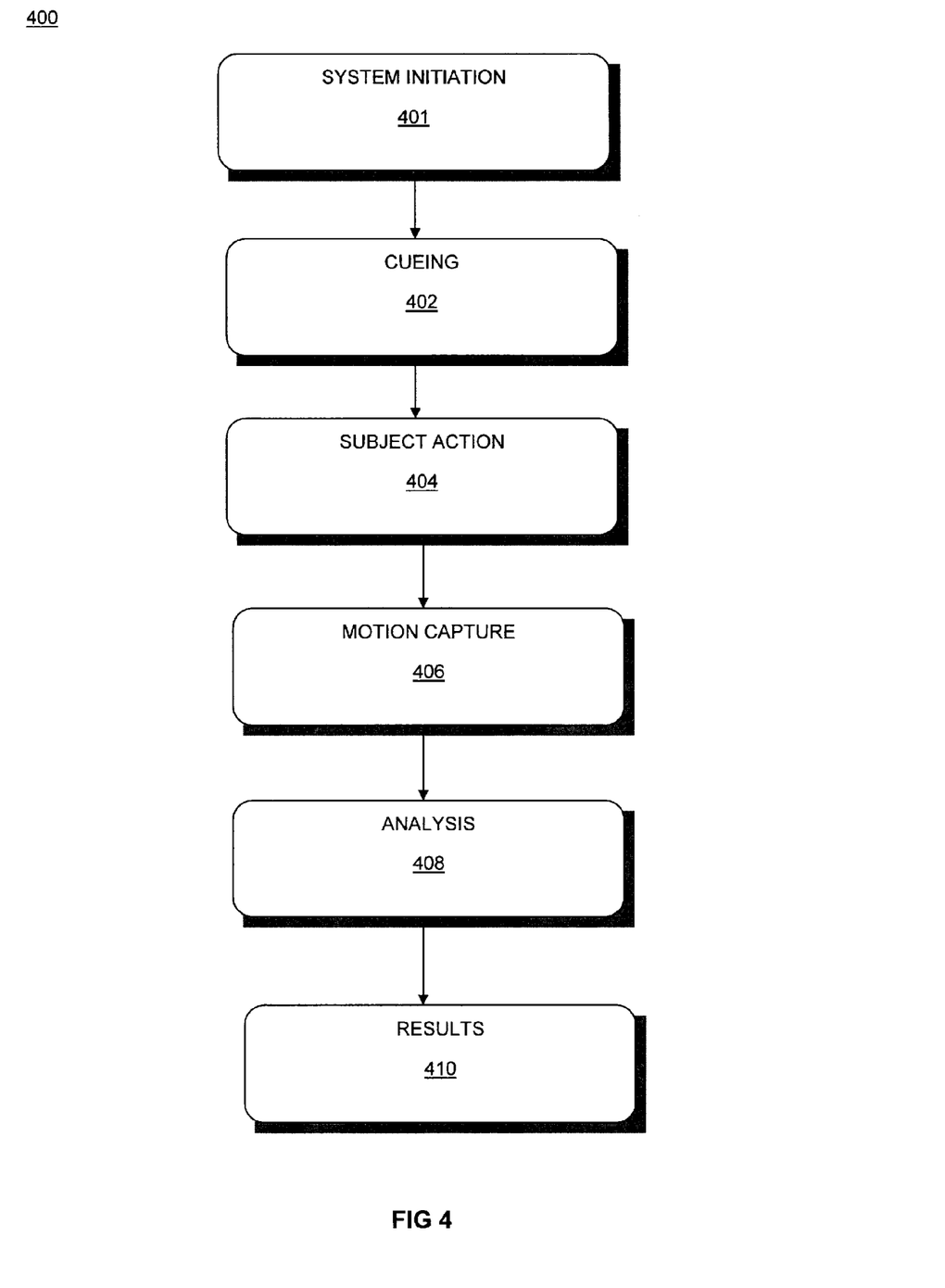
FIG. 4 is a diagrammatic process flow according to one embodiment of a method of the present invention.

FIG. 4 is a block diagram flowchart representing steps of one embodiment 400 of the motion recognition, capture analysis, and tracking system of the present invention. In the method of FIG. 4, a medical researcher initiates the system in block 401. Block 402 represents the system providing a cue, comprising an audible, visual instruction, or both, to the test subject (or patient), such as "spread your fingers". The subject then complies with some action, in block 404, and the system captures the motion 406. Block 408 represents the analysis step. In this step the motion may be analyzed according to a number of protocols, singly or collectively. Motions which may be recorded and analyzed, include, but are not limited to: a range of motion, a speed of motion, acceleration or deceleration of a body part or the entire body, a tremor or vibration, oscillations, rotary or rotational motions, linear motions, a smoothness or fluidity of motion, a direction of motion, radial motions (such as eye motions) a combination of any of the foregoing, and a change in any of the foregoing. The recorded motion or motions may be saved, compared to prior results to arrive at a differential result, or analyzed independently.

Block 410 represents the display of results of the motion capture and/or analysis for the subject or medical researcher, which may further comprise uplinking (or uploading) to a medical researcher or other person in need of the data. The results may be displayed in text or numerical form, in graphic form, or otherwise. A preferred means of display is the avatar presentation, referred to herein. As with the individual subject/patient protocol of FIG. 3, one or more of the cueing compliance and capture steps may be repeated prior to or after the analysis step. In this embodiment, it is contemplated that multiple subjects will be imaged and analyzed, thus the flowchart is repeated for other subjects as many times as deemed necessary or useful by the researcher. The data obtained may comprise an aggregate of all subjects, or may comprise individual subject data. In either case further processing steps can be conducted as desired to look for trends or endpoints.

In one embodiment, presentation of the results utilizes an avatar and body mapping program such as described in the previously described co-pending PCT Patent Application titled: DISPLAY OF CLINICAL RESEARCH DATA USING AN AVATAR. Results may be displayed in one form for the patient and in the same or different form for the healthcare provider/clinician.

It should be noted that certain features, aspects and embodiments identified in the context of the system of either FIG. 3 or FIG. 4 may be equally applicable to the other.

In one preferred embodiment, the medical research data from the plurality of patients is displayed in the form of an avatar, which facilitates display and analysis of multiple patient data. In one aspect, the system provides the ability to superimpose data or move data through time to determine any change in this data. For example, the presentation may include a time slider "soft key" wherein the researcher can look at any time point over the data set.

In one embodiment the avatar display comprises a control which affords the ability to set minimum and maximum range or targets of a given value and to alert or signal when these ranges or levels are met or not met. For example, if a clinician wishes to determine a range of patient motion the system 100 may be set to provide an auditory or visual cue (or both) directing the patient to raised his or her left arm up to the shoulder level. If the patient is able to raise his or her left arm up to the shoulder level, the system may provide an auditory, or visual (or both) feedback, such as "thank you, test completed". In the event the patient is unable to raise his or her left arm up to the shoulder level, the system may then provide a feedback message such as "nice try, let's go to the next test". The system 100 may comprise one or more if (x) then (y) loops, or an artificial intelligence such that certain predefined events can trigger a push of data.

In one embodiment the avatar display comprises an ability to superimpose both computer generated and/or test data and/or actual image data onto the resultant avatar. For example, MRI results, X-rays, CT scan data, or other imaged, analytical or calculated data could be overlaid on the data collected by the motion sensing and capture of the present invention, and displayed on the avatar.

In one embodiment, the system, apparatus and method of the present invention provides to the healthcare provider or clinician or medical researcher the ability to define the level of detail, or granularity of any of the sensed body motion. For example, a researcher could shift focus from the subject's entire body, to an arm, thence to a hand, thence to a finger, and back again.

In one embodiment, the sensing and capture system can be combined with patient data obtained from other sensors, such as cardiac sensors (heart rate, waveforms, blood pressure and the like); oxygen sensors, adherent accelerometers, touch sensors and the like.

Based upon the results of the motion sensing and analysis, treatments, such as therapeutic agents, may be selected by the clinician. Such therapeutic agents for the treatment of multiple sclerosis or a variant thereof include, for example, interferon beta, glatiramer acetate, natalizumab, mitoxantrone, teriflunomide, testosterone, fingolimod, temsirolimus, BHT-3009, MBP-8298, IR-208, CDP-323, BG12 (dimethyl fumarate) cladribine, laquinimod, alemtuzumab (anti-CD52 humanized monoclonal antibody), ocrelizumab (anti-CD20 antibody), ofatumumab, monoclonal antibodies, stem cells, steroids, opiate antagonists, antibiotics, vitamins, statins such as atorvastatin, cerivastatin, fluvastatin, lovastatin, pitavastatin, pravastatin, rosuvastatin and simvastatin, corticosteroids, and combinations of the foregoing. Cholinesterase inhibitors such as donepezil and rivastigmine are suitably selected for diseases such as Alzheimers.

Medications for inflammatory or obstructive airways diseases, such as asthma and/or COPD may be suitably administered. Exemplary active ingredients include long acting beta 2 agonists, such as salmeterol, formoterol, indacaterol and salts thereof, muscarinic antagonists, such as tiotropium and glycopyrronium and salts thereof, and corticosteroids including budesonide, ciclesonide, fluticasone, mometasone and salts thereof. Suitable combinations include (formoterol fumarate and budesonide), (salmeterol xinafoate and fluticasone propionate), (salmeterol xinofoate and tiotropium bromide), (indacaterol maleate and glycopyrronium bromide), and (indacaterol and mometasone).

In some embodiments, the medication or therapeutic agent comprises an immunomodulator. In some embodiments, the immunomodulator comprises fingolimod. In one example, the therapeutic agent comprises a fingolimod distributed by Novartis Pharmaceutical Corporation under the trade name Gilenya™.

In some embodiments, the therapeutic agent or medication comprises a sphingosine 1-phosphate receptor modulator. In some embodiments, the sphingosine 1-phosphate receptor modulator comprises Novartis Pharmaceutical's BAF312.

The foregoing does not in any way limit the therapeutic agents which may be used herewith, as one skilled in the art can readily select, formulate or develop.

In some embodiments, imaging, capture, and measurement of eye movement provides a variety of useful data to the healthcare provider and/or clinician. In one example, the system 100 may take advantage of the relationship between eye movement and neurological function. Thus, the system 100 may cue, via the video display 180 and/or audible command (or both), and instruct a patient to follow with the eye a dot or other icon generated on the video display 180. The dot may be driven by the computer system 140 to move in various patterns, or randomly, on the display 180. Classical eye tests such as the Snellen, Amsler Grid, and Landholt C may readily be administered by the system 100 as the imaging capability of the system 100 affords recognition of patient distance to the video display 180. Moreover, the imaging and motion capture aspects and capabilities of the system 100 enable to system to direct the patient to cover right or left eye, and to verify that the directions are complied with. Thus, for example, the visual acuity may be assessed by any of a variety of visual acuity tests known in the art. Similarly a gaze nystagmus test may be administered and results analyzed.

In one embodiment of the present invention, the system 100 functions as a medication or therapy compliance or adherence device. For example, a patient may be provided with a kit comprising a medicine and a set of instructions to administer the medication while within the motion capture field of the system 100. The set of instructions may be written, may be displayed on the video display 180, or both. In the example of an oral medication, the display may comprise a representation of the medication and a graphic directing administration. The system 100 can thus monitor the patient's self-administration of medicine using the motion sensing, capture and analysis as described herein. The high resolution of the system enables it to differentiate between various types of medications. Failure to take medicine within some prescribed conditions (such as time) can result in a signal being sent to patient's home computer, PDA or cell-phone, smartphone or other wireless mobile device to alert the patient. Similarly successful administration may be used to supply positive feedback, such as a "thank you" message. Where the patient is a child, the system might respond by enabling the child to play a video game. Medicines can comprise oral forms, injections, inhalers and the like. The system 100 could even be programmed to look for and differentiate skin conditions, such as allergic reactions, rash, or the presence or absence of transdermal patches.

In one embodiment, the system 100 may comprise recognition means to recognize, identify and verify the patient or subject. Such means may comprise one or more of facial recognition software, voice recognition software, as retinal scanning or fingerprinting.

In one embodiment of the present invention, the system 100 may function to assess, determine, evaluate and/or monitor sleep disorders or conditions, such as sleep apnea. As described in numerous embodiments, feedback, results, assistance or therapy may be provided to the patient in real-time or near real-time. In the case of sleep apnea, the system 100 may trigger respiratory assistance for the patient, such as a flow of oxygen or air.

In one embodiment of the present invention, the system 100 may function as an assistive device for motion impaired patients. For example, the subject/patient's motion may be captured and translated into effector movement of a robotic assistive device, such as an exoskeleton worn by or fitted to the patient.

In one embodiment, the present invention comprises a medication or therapy compliance or adherence device, e.g. a compliance or adherence kit, comprising (a) a medicine or medication, (b) a motion capture system and optionally (c) a set of instructions to administer the medication within the motion capture system, wherein said motion capture comprises means for motion recognition, capture analysis and tracking, e.g. as herein defined. In one example, the medication comprises an immunomodulator.

In another embodiment, the present invention comprises a tool that can be used as a diagnostic, predictive or therapeutic tool, comprising a motion sensing system and capture system to capture a set of data representing the motions of a person, e.g. as herein above described. Such a tool, e.g. a therapeutic tool, may also comprise a processing system to process said set of data, to yield a set of values associated with said person, e.g. as herein above described; and optionally effector means to translate a set on values into an assistive motion.

In another embodiment, the present invention comprises an assistive device, comprising (a) an imaging means for imaging a motion of a subject, e.g. as herein above described; (b) capture means to capture a set of data representing said motion by said subject, e.g. as herein above described; (c) processing means to process said set of data, to yield a set of values associated with said subject, e.g. as herein above described; and (d) effector means, mechanically linked to said patient and connected to said processing means to translate a set on values into an assistive motion, e.g. as herein above described. Optionally the assistive device can be delivered together with a medication for a disease state comprising a neurological effect or a neurological disorder, e.g. as herein above described.

In another embodiment, the present invention comprises a medication for treating a patient having a disease state comprising a neurological effect, wherein the medication is provided to the patient after the following steps are taken: (a) providing an imaging means for imaging a motion of a patient; (b) providing a capture means to capture a set of data representing said motion by said patient; (c) providing a processing means to process said set of data, to yield a set of values associated with said patient; and (d) providing a feedback means to deliver to said patent and/or caregiver and/or clinician a result of said administration motion.

In some embodiments, there is provided a medication for use in a method for treating a patient having a disease state comprising a neurological effect, e.g. a neurological disorder, wherein said method comprises the steps of: (a) providing an imaging means for imaging a motion of a patient; (b) providing a capture means to capture a set of data representing said motion by said patient; (c) providing a processing means to process said set of data, to yield a set of values associated with said patient; and (d) providing a feedback means to deliver to said patent and/or caregiver and/or clinician a result of said administration motion; and (e) providing the medication responsive to said disease state.

There is provided a medication for treating a disease state comprising a neurological effect in a patient, wherein the medication is provided based upon motion data, and wherein such data are obtained with a method comprising the steps of: (a) selecting one or more patient motions; (b) using a sensing and capture system to image an initial set comprising the one or more selected patient motions to provide an initial set of motion data; and (c) conveying such initial set of motion data to a healthcare provider. The method may further comprises the steps of (d) using the sensing and capture system to image a secondary motion set comprising the one or more motions to provide a secondary set of motion data, the secondary set following a period of time after initiating the therapy; (e) comparing the initial set with the secondary set and conveying the comparison to the healthcare provider.

In one embodiment, the present invention comprises a therapeutic system, e.g. a kit, for the treatment of a disease state comprising a neurological effect in a patient, e.g. a neurological disorder, wherein said kit comprises (a) an imaging means for imaging a motion of the patient; (b) a capture means to capture a set of data representing said motion by said patient; (c) a processing means to process said set of data, to yield a set of values associated with said patient; and (d) a feedback means to deliver, e.g. to said patent and/or caregiver and/or clinician, a result of said administration motion; and (e) a medication for treating said disease state.

The invention is not limited to measuring disease-mediated motion impairment in patients, but can be used equally well to assess (for clinical or other purposes) ranges of motion of various appendages. The sensing and capture system may further be utilized by as an athletic or sports training or assessment tool. In such a case, the target of the imaging is a "subject" rather than patient, and the data collected is provided to the subject (although it could still be uploaded via electronic means to someone other than the subject, such as a trainer or coach).

Embodiments of the present invention may be used for wellness monitoring and/or health maintenance in symptomatic patients or asymptomatic subjects. An exemplary embodiment is the monitoring of elderly subjects for motion-effects of nascent diseases or conditions, such as Alzheimer's, or to coach subjects through exercises intended to be prophylactic.

In any of the foregoing embodiments, results of any of the imaging, video or audio capture, analysis, results, data or presentation may be uploaded to one or more recipients and/or databases. Thus a patient's healthcare provider, clinician or caregiver may receive the data and/or presentation. Additionally or alternatively, the data and/or presentation may be uploaded to a database, such as an electronic health record. Of particular benefit is the combination and/or integration of the imaging, video or audio capture, analysis, results or data with sensor data, patient reported data, adverse event data, biomarker data, patient activity data, such as lifestyle characteristics or combinations thereof. Any such data is preferably associated with a time dimension, so that a historical record may be assembled. From this historical record, predictive, inductive and deductive conclusions may be drawn.

In one embodiment, the system 100 is designed and configured to permit bidirectional feedback. Thus, in such embodiment the results of any of the imaging, video or audio capture, analysis, results, data or presentation are uploaded (or transmitted) to the healthcare provider, and a based upon such results, information can be supplied back to the patient in real-time or near real-time or for later use. The information returned to the patient can comprise any information which may be supplied to a patient by a healthcare provider or laboratory, and may comprise information or directions to take (or refrain from taking) action. For example, the healthcare provider may supply directions to engage in further tests, behavior modification, initiating or changing drug or physical therapy and the like. The steps of obtaining results, providing feedback and taking action may be repeated.

Although a feature may appear to be described in connection with a particular embodiment, one skilled in the art would recognize that various features of the described embodiments may be combined. Moreover, aspects described in connection with an embodiment may stand alone, or may be combined with aspects or elements of other embodiments.

What is claimed is:

1. A touchless system for capturing and evaluating motion data of a subject having a neurological condition, the system comprising:
   (a) a motion database for selecting a subject motion appropriate to the subject's condition;
   (b) a visual display or audio command, to cue the subject to perform the selected motion;
   (c) a plurality of image capture cameras to capture a plurality of images of said motion of said subject wherein said plurality of images comprise a video;
   (d) a processing means to capture a set of image data comprising a depth image representing said motion by said subject wherein said plurality of cameras and said processing means permit detection of a displacement of 0.5 mm;
   (e) data analytic software to analyze at least one said set of data, to yield a set of values associated with said subject; and wherein
   (f) said processing means generates results representative of at least a portion of said processed data, and presents said results in a human-perceivable format.

2. The system of claim 1 wherein the motion data is analyzed by a pattern-recognition algorithm.

3. The system of claim 2 wherein the image capture comprises speckle decorrelation.

4. The system of claim 2 wherein the image capture comprises structured light.

5. The system of claim 1 wherein the motion imaging requires no subject-worn sensor.

6. The system of claim 1 wherein the subject's condition is a neurological disorder which comprises Parkinson's Disease, Multiple Sclerosis or Alzheimer's Disease.

7. The system of claim 1 wherein the subject motion of said video comprises one or more of gait and motor coordination, movement, flexion of limbs, position of limbs, reaction to stimuli, body posture, and physical appearance.

* * * * *